United States Patent [19]
Weaver et al.

[11] Patent Number: 5,397,302
[45] Date of Patent: Mar. 14, 1995

[54] METHOD OF USING A DUAL LUMEN BILIARY CATHETER

[75] Inventors: George W. Weaver, East Earl, Pa.; Harold Jacob, Lawrence, N.Y.; David F. Leighton, West Lawn, Pa.

[73] Assignee: Arrow Precision Products, Inc., Reading, Pa.

[21] Appl. No.: 60,434

[22] Filed: May 11, 1993

Related U.S. Application Data

[63] Continuation-in-part of Ser. No. 880,840, May 11, 1992, abandoned.

[51] Int. Cl.⁶ ............................................. A61M 31/00
[52] U.S. Cl. ..................................... 604/54; 604/264
[58] Field of Search ................ 604/96, 264, 265, 280, 604/49.53, 54; 128/658, 657

[56] References Cited

U.S. PATENT DOCUMENTS

| | | |
|---|---|---|
| 4,592,341 | 6/1986 | Omagari et al. |
| 4,601,713 | 7/1986 | Fuqua |
| 4,671,291 | 6/1987 | Wilson .............................. 128/658 |
| 4,722,344 | 2/1988 | Combron et al. .................. 128/658 |
| 4,781,677 | 11/1988 | Wilcox |
| 4,807,626 | 2/1989 | McGirr |
| 4,893,621 | 1/1990 | Heyman |
| 4,898,591 | 2/1990 | Jang et al. |
| 4,917,667 | 4/1990 | Jackson |
| 4,955,377 | 9/1990 | Lennox et al. |
| 5,084,054 | 1/1992 | Bencini et al. |
| 5,108,416 | 4/1992 | Ryan et al. |
| 5,154,725 | 10/1992 | Leopold |
| 5,167,239 | 12/1992 | Cohen et al. |
| 5,167,623 | 12/1992 | Cianci et al. |
| 5,242,428 | 9/1993 | Palestrant |

OTHER PUBLICATIONS

Arndoreer Inc., pp. 2-7, undated, author unknown.
Microvasive, pp. 1-3, 5/91 Max Force, Biliary Balloon Dilatation Catheters.
RGA Journal, Spring/1988, pp. 199-201, Jerome D. Waye, MD, et al. (Suction Retrieval of the Small Colon Polyp).
Gastrointestinal Endoscopy vol. 38, No. 5, 1992, pp. 531-535, D. A. Howell, MD et al. (Endoscopic needle aspiration biopsy at ERCP in the diagnosis of biliary strictures).
Wilson-Cook Medical Inc., undated, Product Update 1993.

Primary Examiner—Corrine Maglione
Attorney, Agent, or Firm—Amster, Rothstein & Ebenstein

[57] ABSTRACT

A improved biliary catheter is disclosed. The catheter comprises a tube constructed from a polyurethane or nylon having a durometer of about 60D and coated with a hydrophilic coating to provide lubricity, kink resistance and suppleness. The tube has substantially cylindrical sidewalls and a proximal end for connection to a source of contrast medium and a distal end for entry into the common biliary duct of a patient. The tube contains a first crescent-shaped lumen channel extending between the proximal and the distal end, the first lumen channel transporting the contrast medium from the source of contrast medium to the biliary duct; and a second circular lumen channel extending between the proximal end and said distal end for facilitating the insertion and threading of a spring wire guide into the dual-lumen biliary catheter.

14 Claims, 11 Drawing Sheets

METHOD OF USING A DUAL LUMEN BILIARY CATHETER

CLAIM OF PRIORITY

This application is a continuation-in-part of U.S. Ser. No. 07/880,840, entitled Improved Biliary Catheter, filed May 11, 1992, now abandoned.

FIELD OF THE INVENTION

The present invention is directed to the field of Endoscopic Retrograde Cholangiopancreatography (ERCP) catheters. In particular, the present invention is directed to an ERCP catheter which can more easily accommodate spring wire guide insertion and threading as well as contrast media infusion.

BACKGROUND OF THE INVENTION

Endoscopic Retrograde Cholangiopancreatography (ERCP) is an endoscopic technique which involves the placement of a sideviewing instrument within the descending duodenum. The procedure eliminates the need for invasive surgical procedures for identifying biliary stones and other obstructions of the biliary and pancreatic ducts.

Utilizing this technique, the Papilla of Vater and common biliary duct are cannulated, contrast media injected, and pancreatic ducts and the hepatobiliary tree visualized radiographically or examined with a duodeno-fiberscope. Skilled medical practitioners can visualize approximately 90 to 95 percent of the biliary and pancreatic ducts using this technique.

ERCP is typically performed on an x-ray table. During the procedure, the patient's oropharynx is anesthetized with topical lidocaine, and the patient is sedated intravenously with diazepam. Atropine and glucagon are given intravenously to induce duodenal hypotonia.

The ERCP procedure has heretofore typically been performed by the endoscopic introduction of a single lumen catheter into the pancreatic and common biliary ducts of a patient. Such ERCP catheters have typically been constructed from teflon. At times, a spring wire guide may be placed in the lumen of the catheter to assist in cannulation of the ducts. A stylet, used to stiffen the catheter, must first be removed prior to spring wire guide insertion. The introduction of the spring wire guide eliminates the ability to inject contrast media, or makes it highly cumbersome.

To summarize the procedure, an EPCP catheter is initially inserted through the endoscope and into the biliary or pancreatic ducts. If diffficulty is encountered or if the operator so desires, a spring wire guide is threaded into the catheter to assist in the cannulation. After the catheter is inserted into the duct and threaded over the spring wire guide, the spring wire guide is removed. A radio-opaque contrast medium is then injected through the single lumen of the catheter in order to identify obstructions such as bile stones. Once located and identified, such stones can then be eliminated or destroyed by methods such as mechanical lithotripsy, utilizing a device such as Olympus BML-10/20 Mechanical Lithotriptor.

This method of performing ERCP has several disadvantages. Most notably, it relies upon the use of a single lumen catheter which is threaded over the spring wire guide or pushed by a stylet and then, upon the removal of the stylet spring wire guide, used for infusing radio-opaque contrast media or dye into the biliary and pancreatic ducts. Unfortunately, the process of withdrawing the stylet spring wire guide in order to clear the single lumen for contrast media or dye infusion, frequently repositions the Catheter. Thus, when the radio-opaque or contrast media is injected into the catheter, the catheter is often improperly positioned for proper fluoroscopy or x-ray visualization. Moreover, this method presents the further problem of having to repeatedly remove the stylet or an approximate six foot long spring wire guide, maintain its cleanliness and then reinsert it into the catheter. Finally, single lumen catheters frequently experience the problem of back-flow in which the radio-opaque dye is squirted back out the catheter and onto the administering medical professional.

The above problems often result in the need to repeat the procedure, and can lead to a time consuming exercise of trial and error. Multiple attempts at properly positioning the catheter and spring wire guide are often necessary. Because the ERCP procedure is performed under sedation, the additional time required for proper catheter positioning tends to increase the risk to the patient. Furthermore, because of the considerable expense of maintaining a procedure room, the use of single lumen ERCP catheters can add considerably to the expense of the procedure. Accordingly, ERCP procedures have heretofore been performed by only the most skilled endoscopists.

It would be desirable to provide a dual or multi-lumen ERCP catheter in which one lumen could be utilized to accommodate the spring wire guide or diagnostic or therapeutic device, and in which a second lumen could be utilized for contrast media or dye infusion. As noted above, most prior art biliary catheters have been constructed from teflon. While teflon possesses a low coefficient of friction and can be extruded into a catheter having a long passageway, teflon is an unsuitable material from which to construct a multiple lumen catheter for ERCP applications. Because it cannot be extruded properly, attempts at manufacturing a multiple lumen catheter from teflon have resulted in catheters having too narrow a wall thickness.

Furthermore, while other polymers such as polyurethane and polyamide can be extruded to form a dual-lumen catheter for ERCP, most polyurethanes are too soft for ERCP applications and will kink, bunch up or buckle in use. After such kinking occurs, the catheter is rendered inoperative for injecting contrast media or dye.

In view of the above problems, it would be desirable to provide a multi-lumen ERCP catheter in which one lumen may be utilized to inject a contrast media or dye and the second lumen may be utilized for spring wire guide insertion and threading or inserting other devices. It would also be desirable to provide a catheter having calibrated or digitized bands to determine precise points of insertion of the catheter. Such a catheter would facilitate both spring wire guide feeding and adjustment as well as the infusion of contrast media without the need to remove the spring wire guide. Such a catheter would be more hygienic and would further widen the pool of medical professionals who could perform ERCP procedures, and would reduce the time necessary to complete ERCP, thereby reducing the risks to the patient undergoing the procedure. Such a catheter would allow smooth manipulation of the guide wire and simultaneous contrast medium injection. This will result in safer more effective ERCP. Such a catheter may allow cannulation of the right and left hepatic ducts and cystic ducts. Such a catheter would also allow laser lithotripty in the bile duct while the simultaneous injection of contrast medium is taking place.

SUMMARY OF THE INVENTION

In view of the above long-felt need, an improved biliary catheter is contemplated by the present invention. The catheter of the present invention permits the cannulation and radiological examination of the biliary and pancreatic ducts of a patient during ERCP procedures. In a simplest embodiment, the present invention is directed to a biliary catheter comprising a cannula having a proximal end for connection to a source of radio-opaque contrast media to be infused through the cannula and into a common biliary duct of a patient, and a distal end for entry into common biliary duct of a patient such that said radio-opaque contrast media can be infused therethrough. The cannula comprises first lumen means for the introduction and threading of a spring wire guide through the catheter so as to promote insertion of the distal end into the biliary duct, and second lumen means for infusing and transporting said contrast media between said proximal and distal ends.

In a further embodiment, the catheter is constructed from a material having a durometer of about 60D. A key feature of the present invention is the treatment of the catheter with a hydrophilic coating. The hydrophilic coating of the present invention provides a highly lubricated surface which is activated by the biliary fluids of the patient. The hydrophilic coating further functions to soften the material so as to increase the suppleness and kink resistance and lubricity of the catheter, and to reduce its durometer. This coating is applied to the outer surface of the catheter, and may optionally also be applied within the spring wire guide lumen.

In a yet a further embodiment, the catheter comprises a tube having substantially cylindrical sidewalls and having a proximal end for connection to a source of a radiopaque contrast media and for the introduction of a spring wire guide and a distal end for entry into a biliary duct, said tube containing a first crescent-shaped lumen channel extending between said proximal end and said distal end, said first lumen channel transporting a radiopaque contrast medium from said proximal end to said distal end; and a second circular lumen channel extending between said proximal end and said distal end for facilitating the insertion and threading of a spring wire guide into said dual-lumen biliary catheter.

In still yet a further embodiment, the invention is directed to a biliary catheter comprising a tube constructed from a polyurethane or nylon having a durometer of about 60D and coated with a hydrophilic coating to provide kink resistance and suppleness to the polyurethane or nylon, said tube having substantially cylindrical sidewalls and having a proximal end for connection to a source of contrast media and a distal end for entry into a biliary duct; said tube containing a first crescent-shaped lumen channel extending coaxially between said proximal and said distal end, said first crescent-shaped lumen channel transporting said contrast medium from said source of contrast medium to said biliary duct; and a second circular lumen channel extending between said proximal end and said distal end for facilitating the insertion and threading of a spring wire guide into said dual-lumen biliary catheter.

The present invention further includes means for locking the position of the guide wire. In addition, the present invention includes a calibrated tip which may be recessed.

The present invention can be used for numerous ERCP applications and is particularly suited for simultaneous guidewire manipulation or stent placement with ongoing injection of contrast media. These and other features and advantages of the present invention will become clear from the following detailed description.

DETAILED DESCRIPTION OF THE PREFERRED EMBODIMENT

Figure 1:
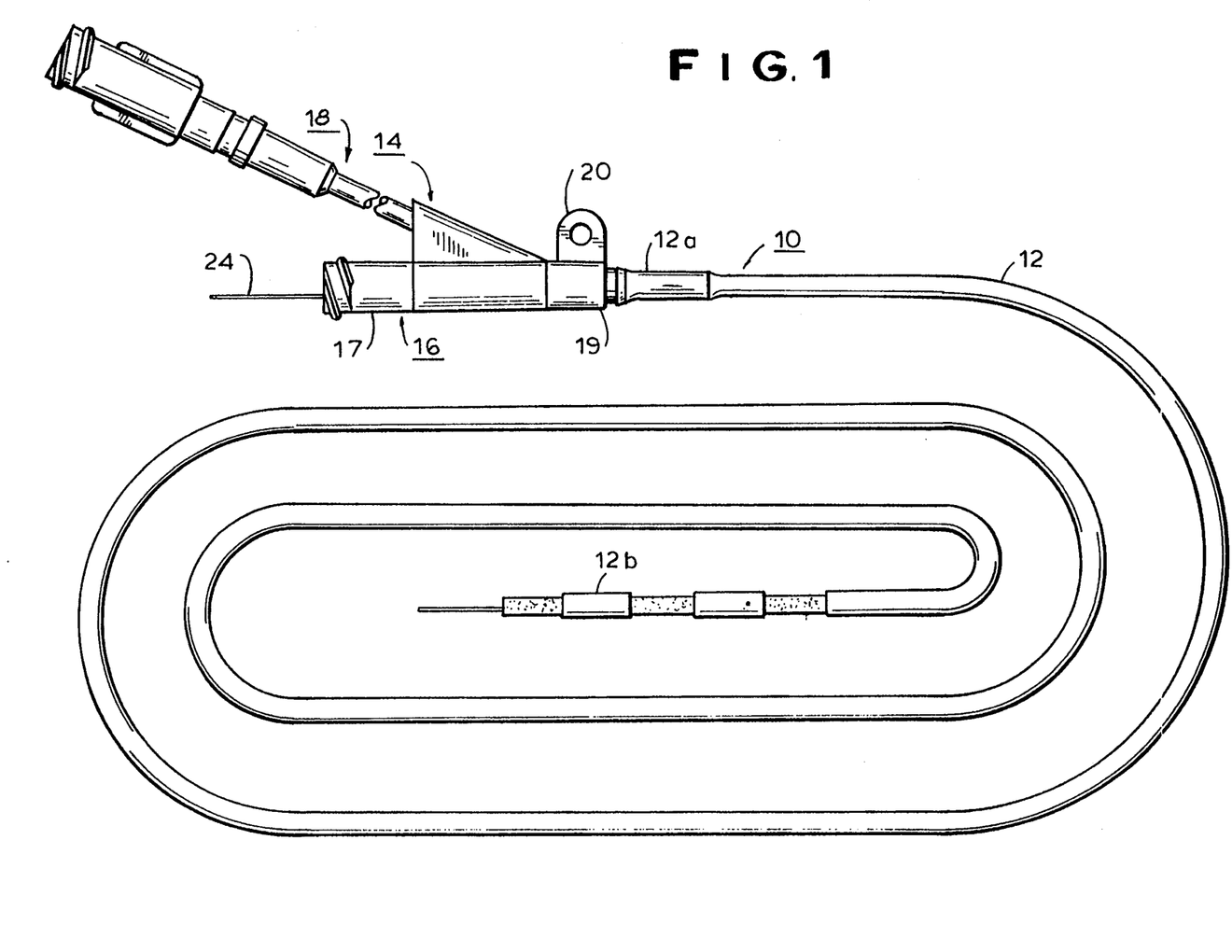
FIG. 1 is a perspective view of the dual-lumen biliary catheter of the present invention.

The improved biliary catheter of the present invention is described with reference to the enclosed Figures wherein the same numbers are utilized where applicable. For the purposes of description, the present invention will be described in the context of its use in the cannulation and visualizing of the common biliary duct of a patient pursuant to an ERCP procedure. It is to be recognized that the present invention is applicable to all ERCP procedures involving the cannulation and radiological visualization of the common biliary, pancreatic, common hepatic and cystic ducts. Referring to FIGS. 1 to 5A, a biliary catheter 10 in accordance with the present invention is illustrated. Referring to FIG. 1, in a preferred embodiment, the catheter of the present invention comprises a cannula or tube 12 having a proximal end 12a for connection to a source of contrast media and a distal end 12b for insertion into the biliary duct of a patient. Tube 12 has a substantially circular cross-sectional shape. Tube 12, in a preferred embodiment, has a length of approximately 200 centimeters. This length permits the catheter 10 to be inserted endotracheally into a patient via an endoscope and reach biliary and pancreatic ducts located adjacent the patient's duodenum via an attached fiberscope during an ERCP procedure.

Figure 2:
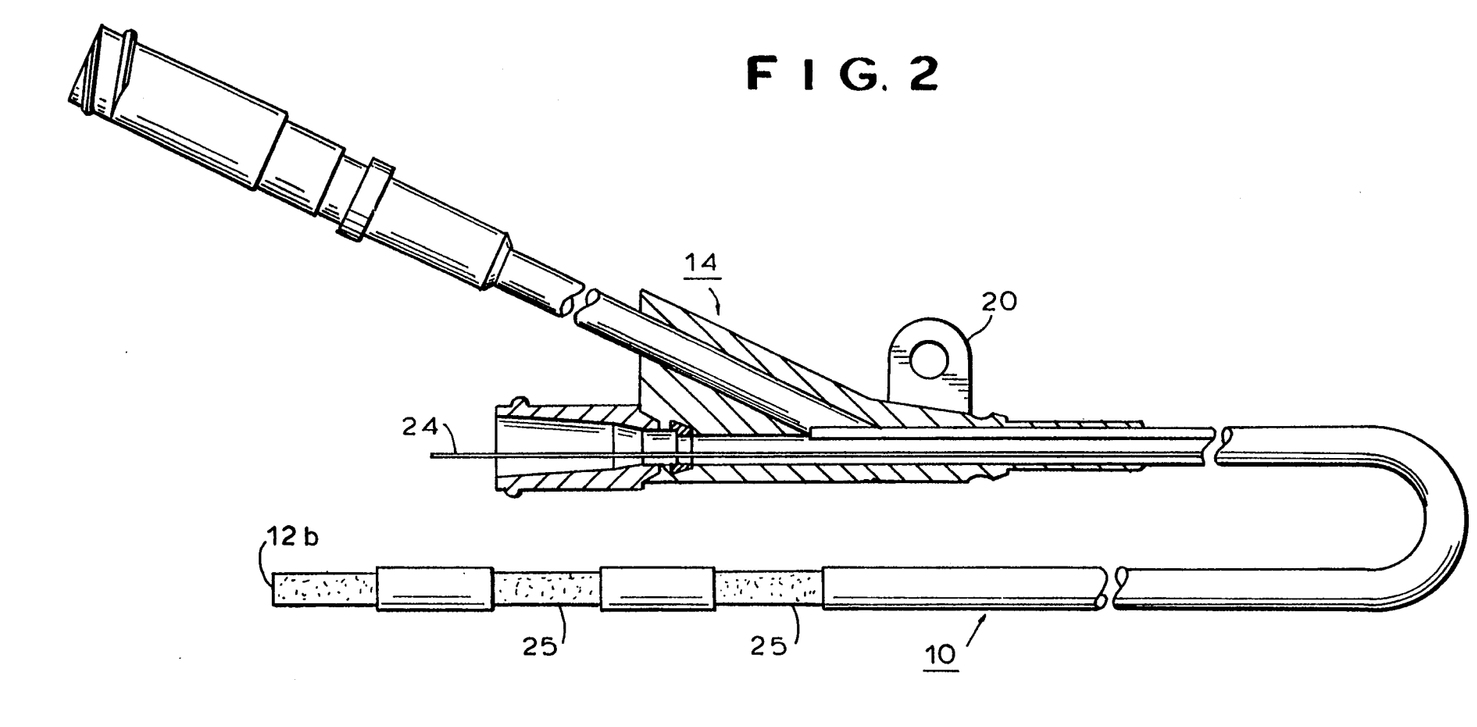
FIG. 2 is a partially broken away section view of the dual-lumen biliary catheter of the present invention.
Figure 4:
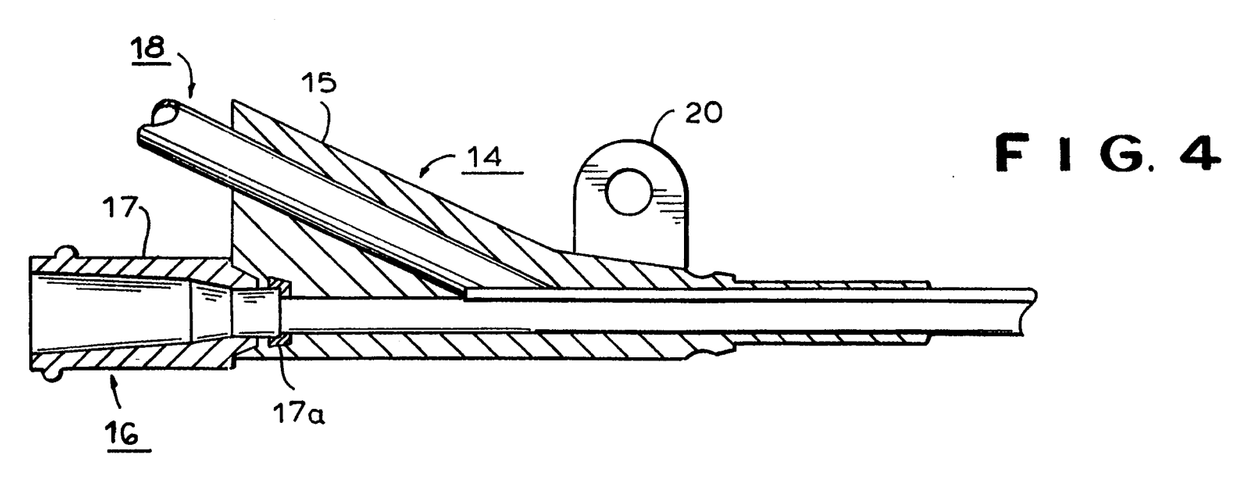
FIG. 4 is a section view of the branching connector which joins the spring wire guide infusion line and contrast medium infusion line of the present invention.

The proximal end 12a of tube 12 attaches to branching means 14 which couples the tube 12 to spring wire guide feeding means 16 and contrast medium infusion means 18. In a preferred embodiment as shown in FIGS. 1, 2 and 4, branching means 14 comprises a wedge-shaped polymeric branching connector 15 which joins the spring wire guide feeding means 16 and contrast medium infusion means 18. The branching connector 15 may include a connector 19 having an affixed apertured wing 20.

Referring to FIGS. 1 and 4, the spring wire guide feeding means 16 in a preferred embodiment comprises an eighteen gauge luer lock hub 17 which couples to the branching means 14 via a dovetail socket 17a. The spring wire guide feeding means 16 is utilized to feed a spring wire guide 24 into and out of the catheter 10. The spring wire guide utilized in a preferred embodiment should have a diameter of 0.035 inches. The use of a spring wire guide having this diameter permits the spring wire guide to be used for placing an indwelling stent, to be discussed below.

Figure 10:
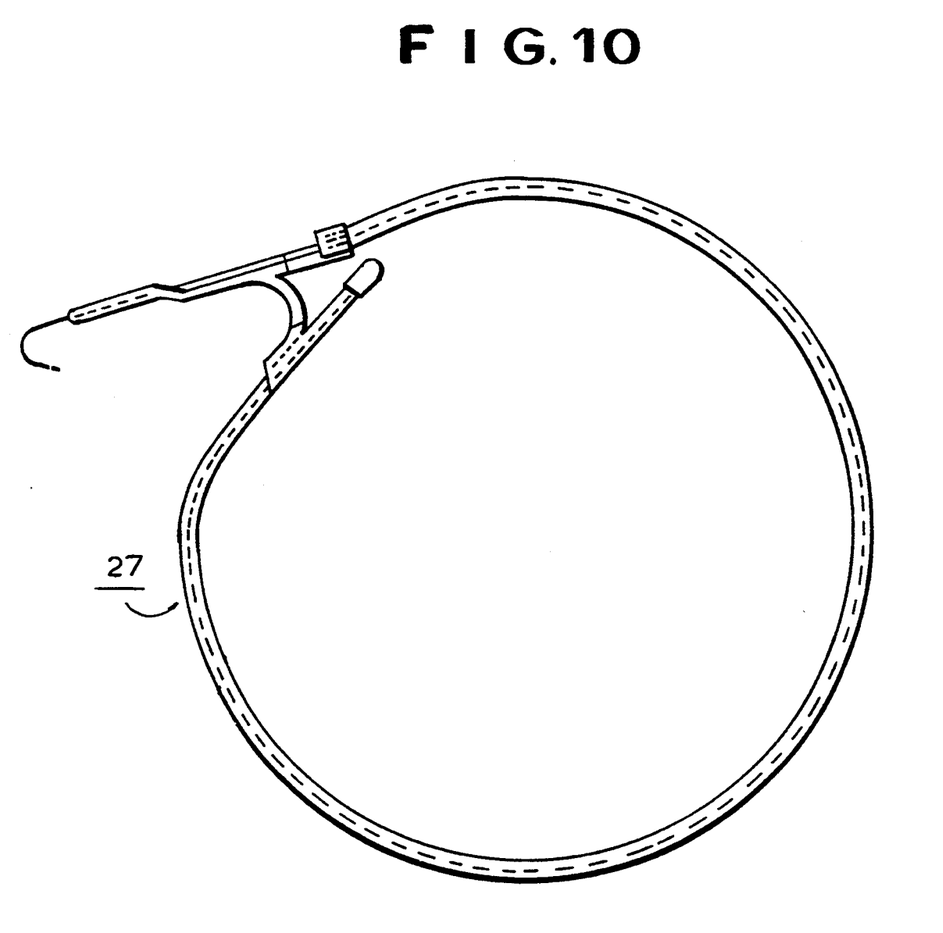
FIG. 10 is a side perspective view of spring wire guide feed apparatus which may be utilized with the present invention.
Figure 10A:
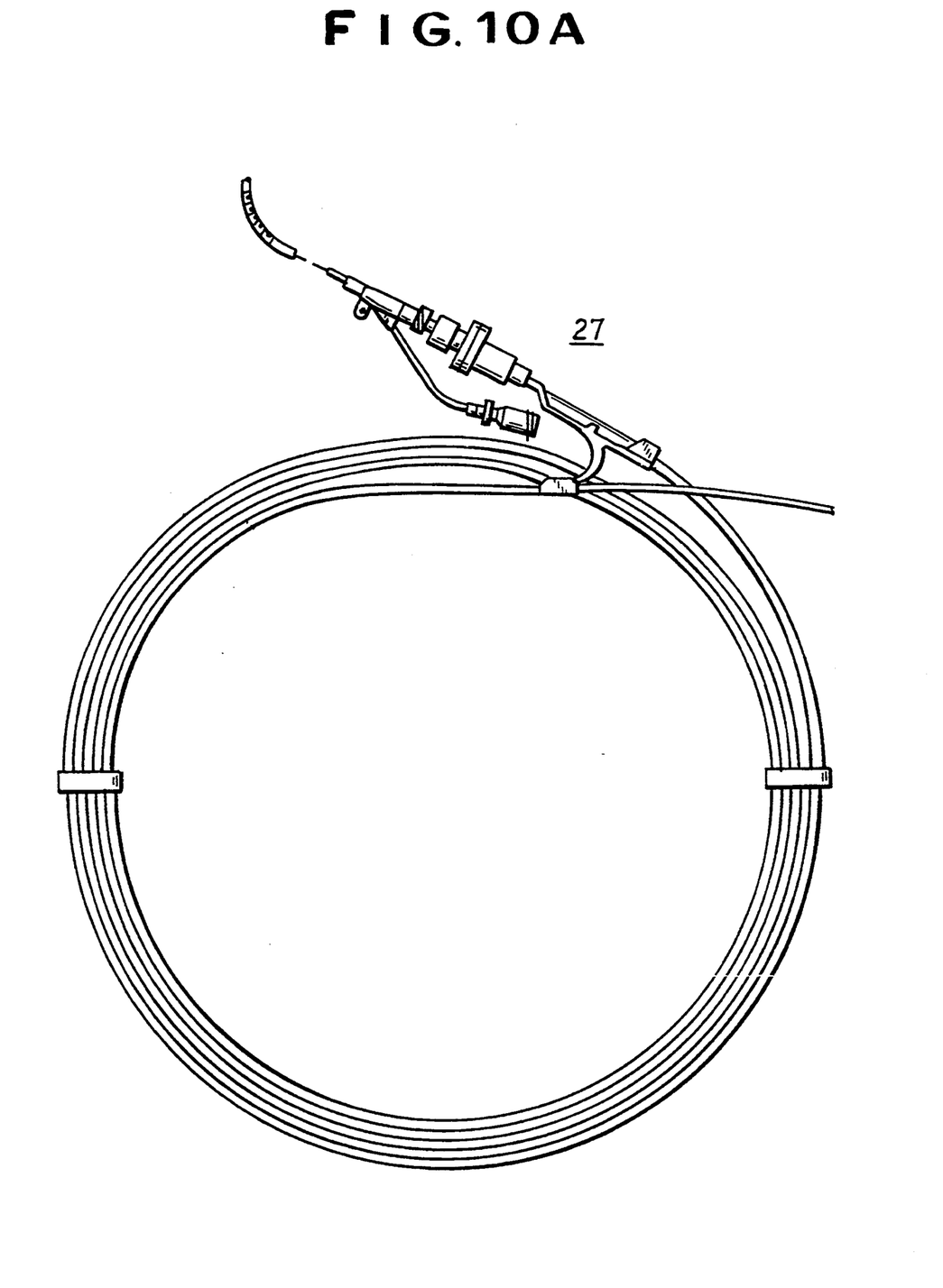
FIG. 10A is a side perspective view of an alternative spring wire guide feed arrangement including a snap lock adapter which may be utilized with the present invention.
Figure 13A:
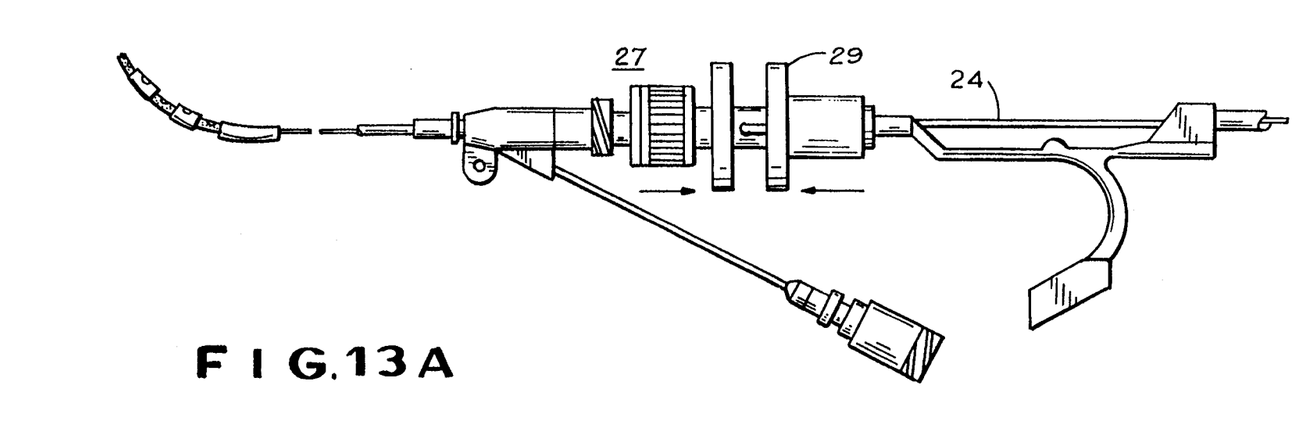
FIGS. 13A and 13B illustrate the alternative feed mechanism of FIG. 10A including guide wire locking mechanism.
Figure 13B:
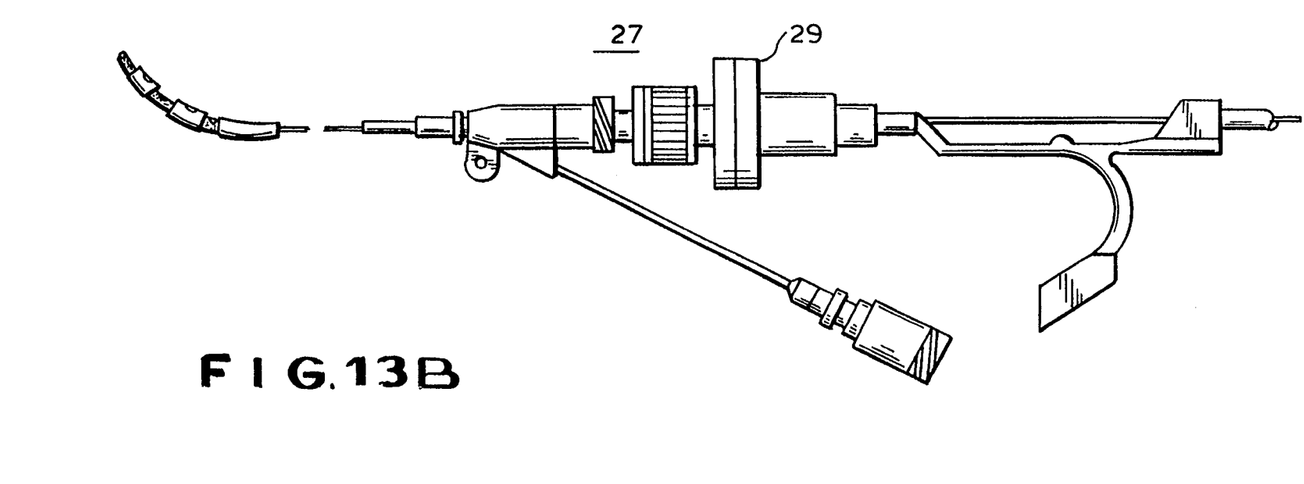
Figure 14:
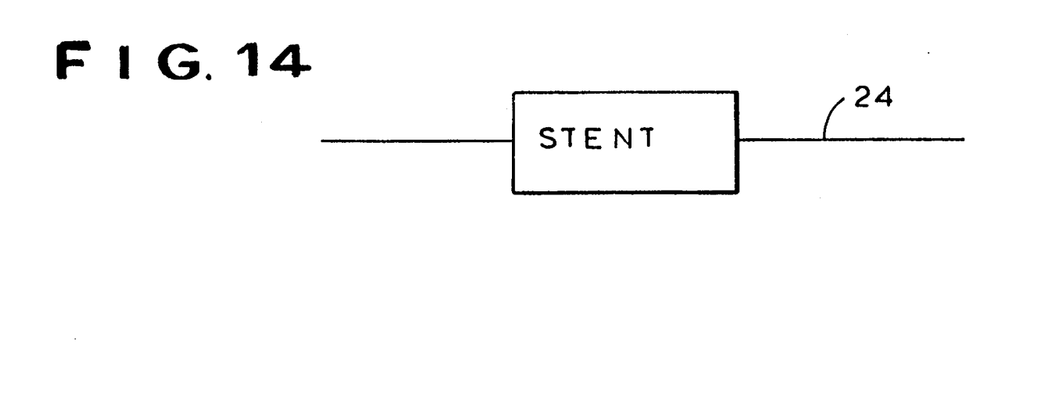
FIG. 14 shows a conventional stent threaded over a spring wire guide.

The spring wire guide 24 may optionally be coated with teflon in order to add to its lubricity. The spring wire guide of the present invention may further be fed and withdrawn with the assistance of an auxiliary apparatus such the spring wire guide feed apparatus disclosed in U.S. Pat. No. 5,125,906 entitled "Hand Held Device For Feeding A Spring Wire Guide", which is incorporated herein by reference as if set forth in full. A perspective view of such a device 27 is illustrated in FIG. 10. In an alternative embodiment shown in FIGS. 10A, 11A and 11b the wire guide feed device 27 is affixed to snap lock adapter 29 for locking the position of the wire. FIGS. 13A and 13B illustrate the respective unlocked and locked positions of the adapter.

Figure 5:
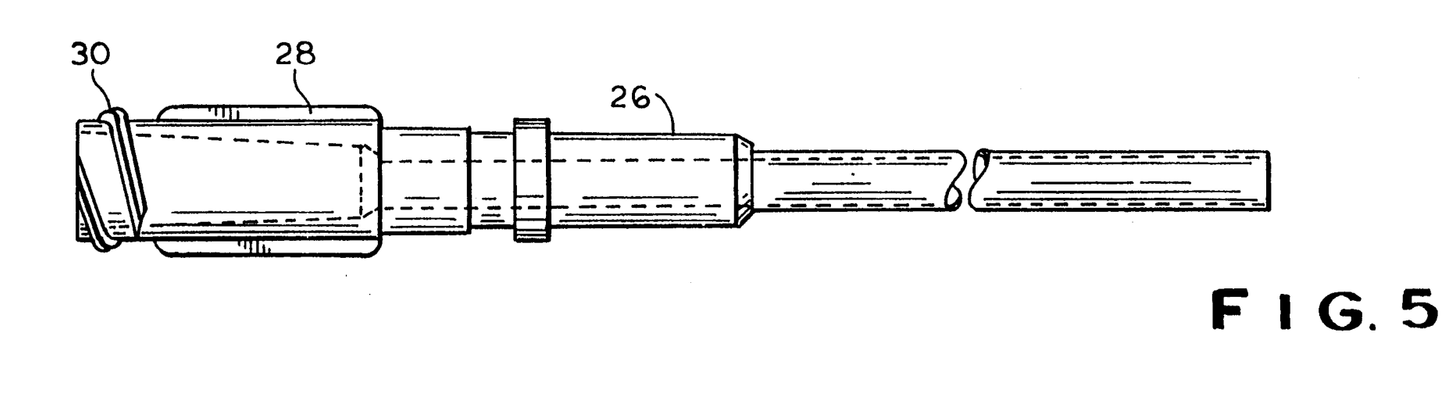
FIG. 5 is a perspective view of the contrast medium infusion line of the present invention.
Figure 5A:
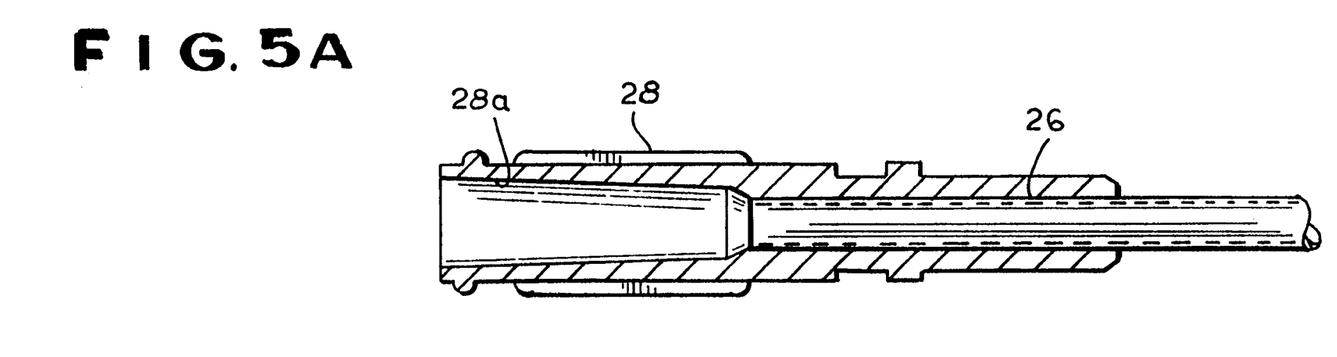
FIG. 5A is a section view of the contrast medium infusion line of FIG. 5.

Referring to FIGS. 1, 2, 5 and 5A, the contrast medium infusion means 18 in a preferred embodiment preferably comprises a polymeric tube 26 which couples to a twenty-gauge connector 28. The connector 28 has a threaded outer surface 30 onto which may be affixed a cap or stopper (not shown). As shown in FIG. 5A, the interior 28a of the connector 28 is luer shaped and is designed to be coupled to a syringe containing radio-opaque contrast media or dye. The contrast media or dye is injected down tube 26 and into a contrast media lumen 34 to be discussed below.

Figure 3:
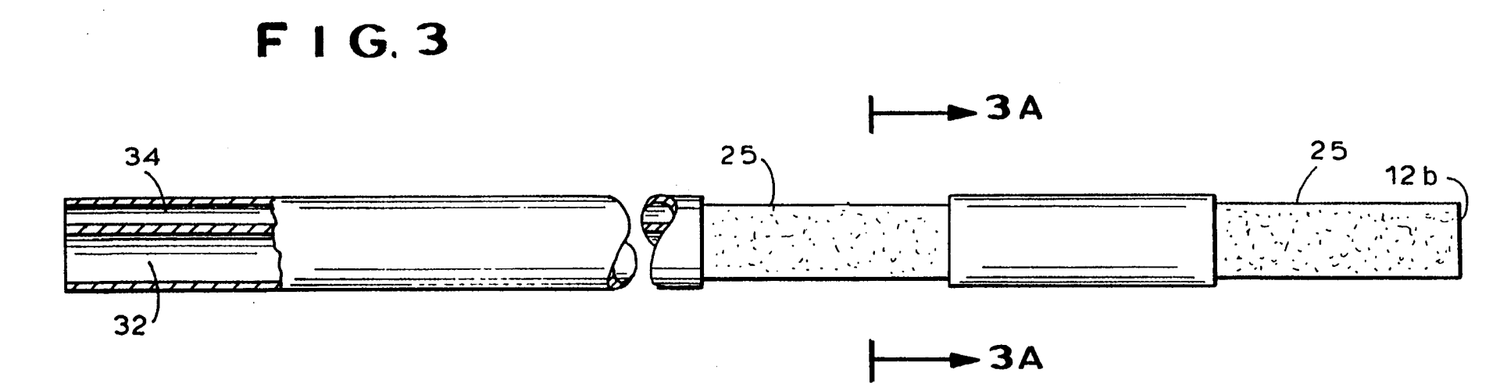
FIG. 3 is a perspective view of the dual-lumen biliary catheter of the present invention which highlights the contrast stripes at the distal end of the catheter.
Figure 11A:
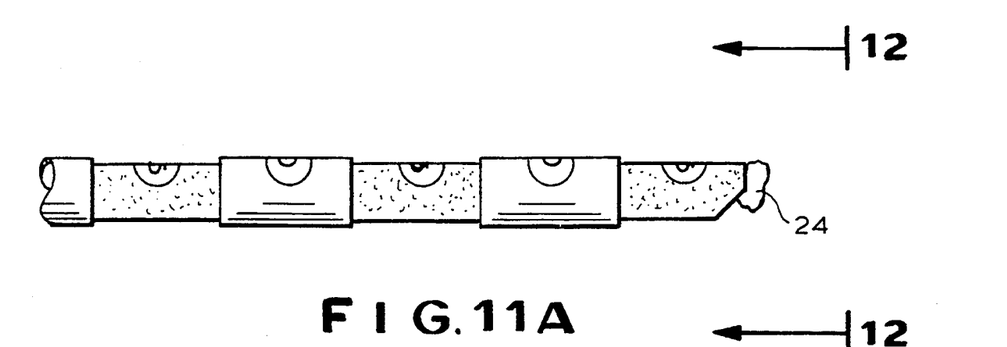
FIGS. 11A and 11B are side views of a catheter of an alternative embodiment having a tapered tip and digitized markings.
Figure 11B:
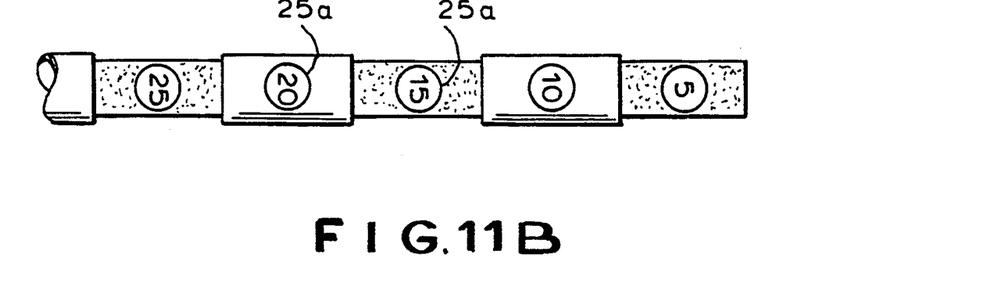
Figure 12:
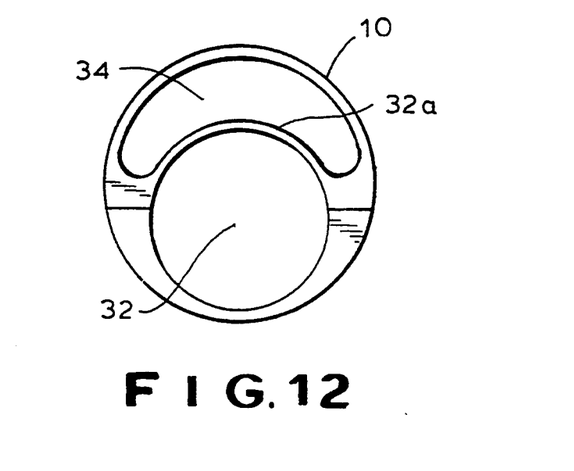
FIG. 12 is a section view of the catheter of FIG. 11A along line 12—12.

Referring to FIGS. 2 and 3, the distal end 12b of the tube 12 is shown in detail. The distal end of the catheter 12b includes means 25 for contrasting the outer distal surface of catheter radio-opaque. Contrast means 25 facilitates the visual identification of the distal end of catheter 10 by the endoscope. In a preferred embodiment, means 25 comprises a plurality of non-toxic ink stripes 25 such as sold under the specification LON-1342 by Colorcon, Inc. of West Point, Penn. It is to be appreciated that contrast stripes 25 comprising other materials may be utilized in the biliary catheter of the present invention. Moreover, it is to be appreciated by those skilled in the art that the entire catheter 10 or portions thereof may be or applied with any acceptable contrast medium. As shown in FIGS. 11A and 11B, the tip 12b of the catheter may be calibrated 25a at predetermined intervals such as five millimeters. In this embodiment catheter tip 12b is tapered to facilitate ease of insertion of the guide wire. It is also to be appreciated that the catheter tip may be curved to facilitate entry of the guide wire.

Figure 3A:
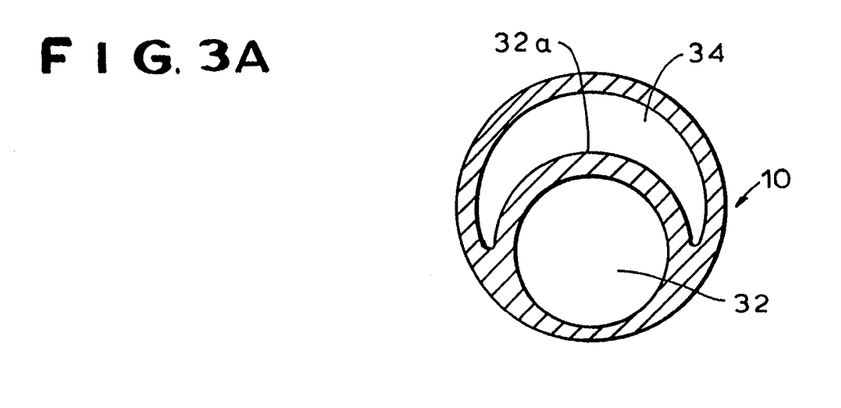
FIG. 3A is a section view highlighting the dual lumens of the biliary catheter of the present invention along line 3A—3A.

Referring to FIGS. 3 and 3A, the lumens 32, 34 of catheter 10 of the present invention are shown so as to detail their cross-sectional shape. In a preferred embodiment, the catheter 10 includes a spring wire guide lumen means 32 and contrast media lumen means 34. In a preferred embodiment, the lumen means 32, 34 extend coaxially within the tube 12 along its entire length between the proximal end 12a and distal end 12b. Referring to FIGS. 8, 11, 11A and 12 alternative distal end 12b is shown tapered with the contrast media lumen means 34 terminating proximal of the spring wire guide lumen means 32.

Spring wire guide lumen means 32 is circular in cross-section. The top of spring wire guide lumen 32 is defined by an arcuate septum 32a which defines the interior sidewall of the contrast medium lumen 34. In a preferred embodiment, contrast medium lumen 34 is crescent-shaped. While the present invention is described in the context of a biliary catheter having dual lumens, it is to be appreciated by those skilled in the art that the present invention embodies catheters having more than two lumens. Further, while the present invention is described with respect to a contrast media lumen 34 having a crescent shape, it is to be appreciated that the present invention also embodies catheters in which the contrast media lumen may assume one of a plurality of geometric shapes.

The catheter 10 of the present invention is preferably constructed from a polyurethane or nylon having a durometer of about 60D or greater. One polyurethane known to be suitable in the present invention is a polyether-polyurethane called TECOFLEX sold under part number EG-60D-B20 by Thermedics. This material has a hardness of 60D, a yield elongation percentage of 275 to 475 and a yield tensile strength in pounds per square inch of 5,000. In a more preferred embodiment, the resin of the present invention comprises a mixture of 20% barium sulfate, 60% Nylon 11 BESVOA and 20% PEBAX, polyether block amide (12055A00). Nylon II BESVOA and PEBAX are manufactured by Atochem.

A further important feature of the present invention is the addition of a hydrophilic coating on the outer surface of the catheter 10 and optionally within the spring wire guide lumen 32. The hydrophilic coating when applied to the catheter, imparts suppleness and kink resistance to the catheter. The hydrophilic coating further reduces the durometer of the polyurethane or nylon. The hydrophilic coating of the preferred embodiment comprises the following components: (a) 150 milliliters of Methylene Chloride (MeCl); (b) 50 milliliters Gensolv D DuPont Freon Solvent: (c) 2.25 milliliters Tyrite 7617 Adhesive, and (d) 2.13 grams of Polyethylene Oxide (PEO).

The hydrophilic coating of the preferred embodiment is applied to the catheter pursuant to the following process. Initially, 150 milliliters of MeCl is poured into a beaker. Next, 50 milliliters of Gensolv D is added, and the beaker is placed on stirrer plate. A stirring magnet is then dropped into the beaker and the stirring plate is activated. Stirring is adjusted until a vortex forms. Next, 2.13 grams of PEO are slowly added to the stirring solution. The solution is stirred continuous for 10 minutes, in order to break up any lumps of PEO. Using a syringe, Tyrite 7617 adhesive is added to the stirring solution, which is permitted to stir for an additional five minutes. The stirred solution is then poured into a 200 milliliter graduated cylinder.

The catheter 10, with its end sealed off, is then dipped into the cylinder until it reaches the bottom of the cylinder. The catheter 10 is left in the cylinder for 2-3 seconds, quickly retrieved and the excess solution shaken off. The catheter is then air-dried for a minimum 24 hours. As an optional step, after the catheter is air-dried for 24 hours, solution may be injected down the spring wire guide lumen 32 of the catheter. Air is blown through the lumen immediately to drive out excess solution. Air is blown through the catheter for three to five minutes, and the catheter is left to dry for a minimum of 24 hours.

The catheter 10 with hydrophilic coating provides a highly lubricated surface which is activated by the biliary fluids of the patient. The hydrophilic coating may also be activated by the gastric fluids which enter the endoscope. The hydrophilic coating reduces the durometer of the catheter, and imparts kink resistance and suppleness to the catheter.

While the present invention is being described in the context of a preferred hydrophilic coating, it is to be appreciated that other hydrophilic coatings may be utilized in the present invention. Examples of such hydrophilic coatings are found and described in U.S. Pat. No. 4,943,460 entitled "Process for Coating Polymer Surfaces and Coated Products Produced Using Such Process." Another hydrophilic coating is Hydromer®"Slippery When Wet" coating manufactured by Hydromer, Inc.

Figure 7:
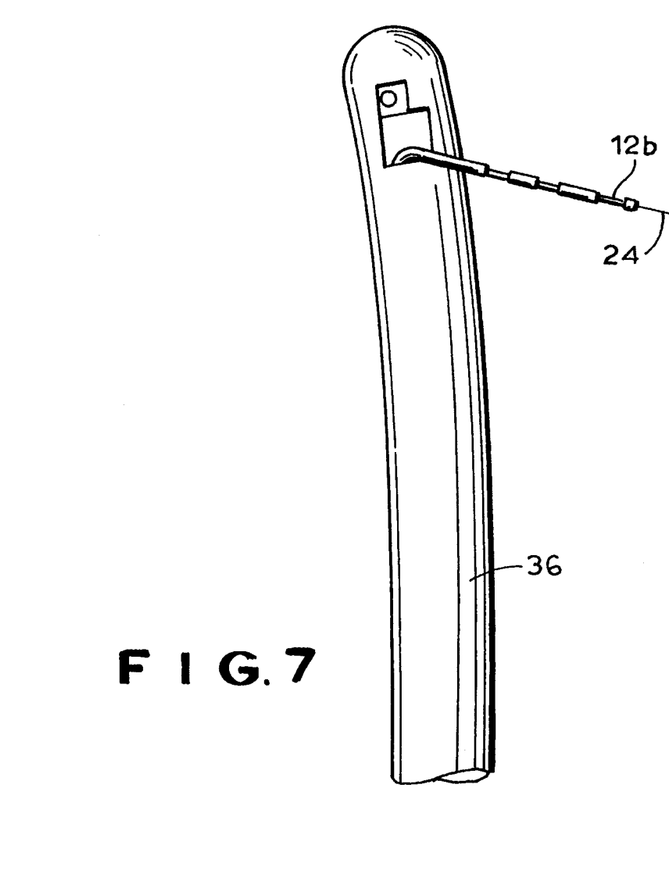
FIG. 7 illustrates the use of the dual-lumen catheter of the present invention with a fiberscope.
Figure 8:
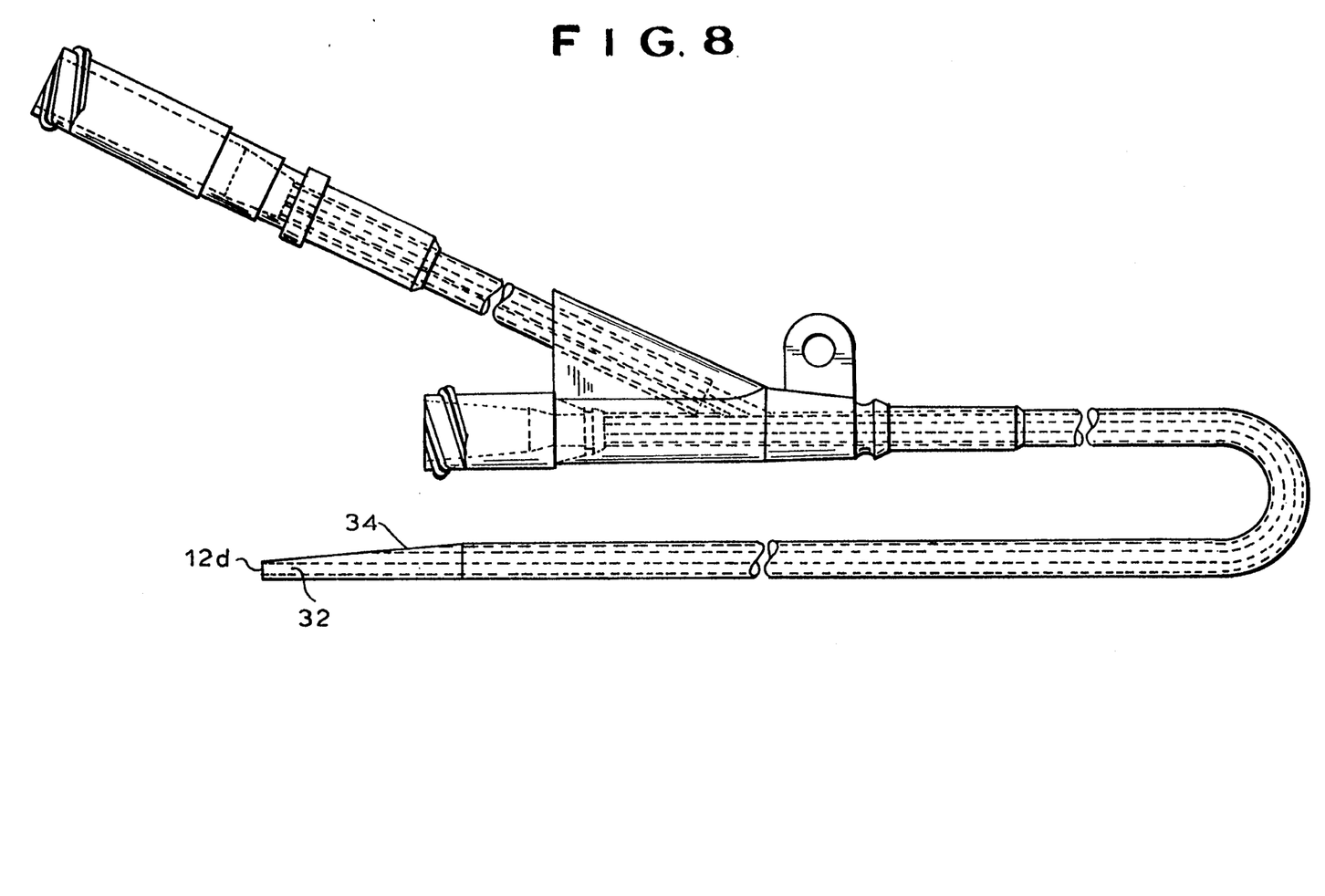
FIG. 8 is a section view of an alternative distal tip configuration for the biliary catheter of the present invention.

The operation and use of the biliary catheter 10 of the present invention is now described with reference to the Figures. Initially, the patient is sedated, or in rare situations, placed under general anesthesia. The spring wire guide 24 is inserted through an endoscope and exits through the side of an attached fiberscope 36 as shown in FIG. 7 situated in the patient's duodenum 38. The catheter 10 is then threaded over the spring wire guide 24 via spring wire guide lumen 32 and fed through the fiberscope 36 and into the common bile duct 40.

Figure 6:
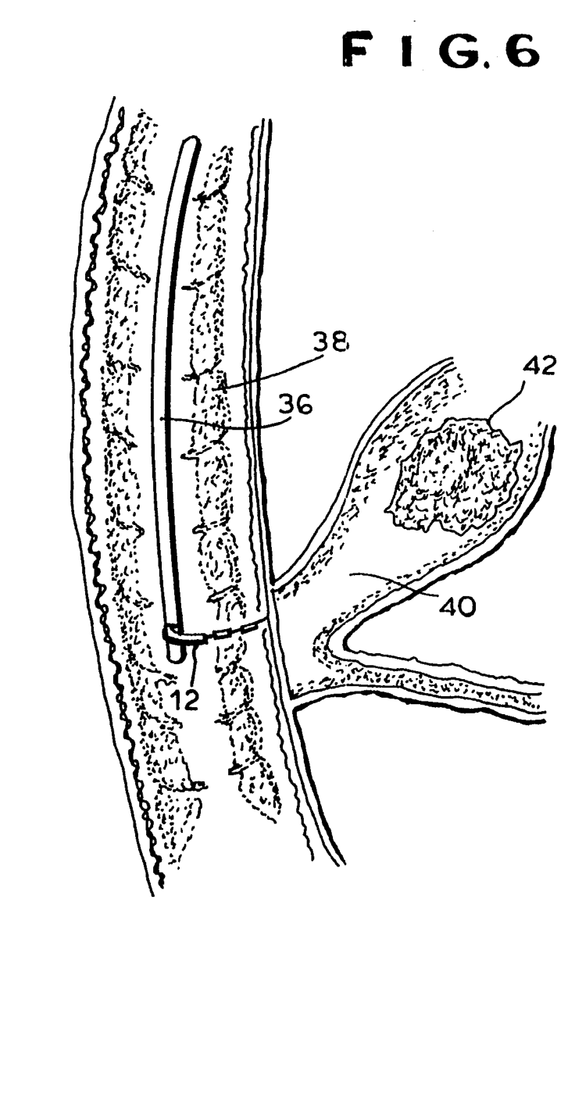
FIG. 6 illustrates the introduction of the catheter of the present invention into a common biliary duct.
Figure 9:
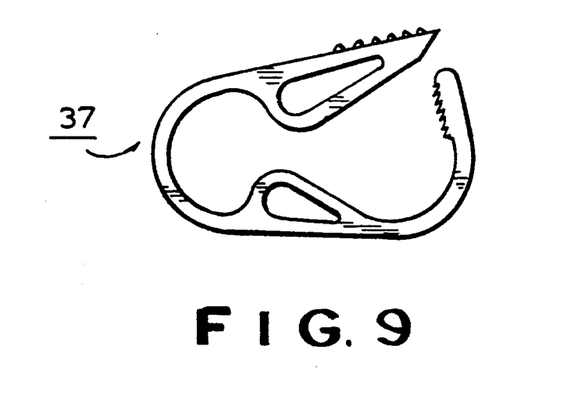
FIG. 9 is a section view of tubing clamp which may be utilized in the present invention to lock the relative positions of the catheter and spring wire guide which may be utilized with the present invention.

Next, a pre-filled syringe of radio-opaque dye or contrast media is attached to twenty-gauge luer shaped connector 28. A sufficient amount of dye to fill the catheter is then injected into tube 26. The catheter 10 is inserted through the accessory channel of the endoscope and threaded over the spring wire guide 24 via lumen 32. The catheter 10 exits the side of the fiberscope and enters the common bile duct, as shown in FIGS. 6 and 7. Referring to FIG. 9, clamp 37 may be used to lock the relative positions of the catheter and spring wire guide. An example of clamps which achieves this function are the Series 340 clamps by Halkey Medical of St. Petersburg, FLA. Contrast media is then injected into the contrast medium lumen 34 which exits at distal end 12b and into the common biliary duct 40 thereby permitting x-ray or fluoroscopic visualization of the duct 40. Markings 25a facilitate precise adjustment of the catheter. If the position of the catheter needs to be adjusted, the spring wire guide 24 is advanced and the catheter 10 advanced accordingly. The catheter can be rapidly adjusted and contrast media and dye can be repeatedly infused without the need for repeated insertion and removal of the spring wire guide 24.

The present invention thus provides for the probing with the spring wire guide 24, the injection of dye or contrast media, via contrast media lumen 34, further probing, and further injection of dye until a proper catheter position is achieved. The present invention eliminates the time consuming step of removing the spring wire guide 24 prior to each change in catheter position and contrast medium infusion. The use of the catheter of the present invention can save over twenty minutes of time during a typical ERCP procedure. In addition, a laser fiber for biliary lithotripty can be placed through one lumen with ongoing injection of contrast medium or fluid in the second lumen. Further, selective cannulation of the right and left hepatic ducts, cystic ducts, or pancreas becomes more directed, safe and efficient.

A particular feature of the present invention is its adaptability for use in placing a stent around a biliary calculus 42 or cystic or pancreatic obstruction. In approximately five percent of all ERCP cannulations, surgery is mandated. However, surgery is often not always possible at the time of the ERCP procedure. In such situations, a stent is typically placed within the common biliary or pancreatic duct around the calculus.

As used in such an application, the catheter 10 is utilized in association with a spring wire guide 24 having a length greater than twice the length of the catheter 10, or over 400 centimeters in length. The spring wire guide would be threaded with the catheter into endoscope as described above. The spring wire guide should preferably have a diameter of 0.036 inches.

The catheter 10 of the present invention is then threaded over the spring wire guide as discussed above, and fed into the common biliary duct. Contrast media or dye is infused, and the calculus 42 is located as shown in FIG. 6. The catheter 10 is then removed from the endoscope.

Because the spring wire 24 guide has a length greater than twice that of the catheter 10, the catheter 10 can be completely removed from the endoscope over the spring wire guide 24 without the need for removing the spring wire guide from the endoscope. After the catheter 10 is removed, a stent may be placed forward of a guiding catheter and is threaded over the spring wire guide. The guiding catheter is utilized to push the stent into the endoscope, over the spring wire guide, into the common biliary duct and around the biliary calculus 42. With the stent in place, the spring wire guide 24 is then removed along with the guiding catheter. It is to be appreciated by those skilled in the art that other accessories such as stone baskets, three pronged retrievers and fiber optic cameras can be used interchangeably in the first lumen with the guide wire.

The present invention has been described with reference to the attached Figures and described embodiments. It is to be appreciated that other embodiments may fulfill the spirit and scope of the present invention and that the true nature and scope of the present invention is to be determined with reference to the claims appended hereto.

What is claimed is:

1. A method for placing a catheter and a contrast medium into a duct of a patient, said catheter having at least a first lumen and a second lumen, and said first lumen having a wire guide threaded therethrough, comprising the steps of:
    inserting said catheter and said wire guide through an endoscope and into said duct;
    infusing said contrast medium through a second lumen of said catheter and into said duct while said wire guide remains in said first lumen such that said duct may be visualized through the use of said contrast medium.

2. A method for placing a catheter and a contrast medium into a duct of a patient, said catheter having at least a first lumen and a second lumen, each terminating in a distal opening at a distal tip of said catheter, said first lumen having a wire guide threaded therethrough, comprising the steps of:
    inserting said catheter and said wire guide through an endoscope and into said duct;
    infusing said contrast medium through a second lumen and through said opening defined in said catheter at said distal tip of said catheter and into said duct while said wire guide remains in said first lumen of said catheter and said dual lumen catheter remains Within Said endoscope such that said duct may be visualized through the use of said contrast medium.

3. A method according to claim 2 for adjusting the position of said distal tip of said catheter in said duct of said patient and visualizing said duct after said adjustment, further comprising the steps of:
    advancing said wire guide through said first lumen and said respective opening defined in said distal tip of said catheter and along said duct;
    advancing said catheter along said wire guide and along said duct to a desired position within said duct;
    infusing said contrast medium through said second lumen and said respective opening defined in said distal tip of said catheter and into said duct while said wire guide remains in said first lumen of said catheter to visualize said duct through the use of said contrast medium.

4. The method according to claim 3 which further includes the additional steps of:
    further advancing said wire guide through the distal end of said first lumen and along said duct,
    further advancing said catheter along said wire guide and along said duct to a second desired position within said duct,
    infusing additional contrast medium through said second lumen of said catheter and visualizing said duct through the use of said contrast medium.

5. A method for placing a dual lumen catheter and a contrast medium into a biliary duct, said dual lumen catheter having a distal tip and defining at least one distal opening at said distal tip, comprising the following steps:
    threading a wire guide through a first lumen of said dual lumen catheter;
    inserting said dual lumen catheter and wire guide through an endoscope and into a biliary duct;
    infusing said contrast medium through a second lumen and through said opening defined in said dual lumen catheter at said distal tip of said dual lumen catheter and into said biliary duct while said wire guide remains in said first lumen of said dual lumen catheter and said dual lumen catheter remains within said endoscope such that said biliary duct may be visualized through the use of said contrast medium.

6. A method according to claim 5 wherein said contrast medium comprises a radio-opaque medium and said biliary duct is visualized radiologically.

7. A method for placing a dual lumen catheter and a contrast medium into a biliary duct, said dual lumen catheter having a first lumen and a second lumen, and defining at least one distal opening at a distal tip of Said catheter, said first lumen having a wire guide threaded therethrough, comprising the steps of:
    inserting said dual lumen catheter and wire guide through an endoscope and into a biliary duct;
    infusing said contrast medium through a second lumen and through said opening defined in said dual lumen catheter at said distal tip of said dual lumen catheter and into said biliary duct while said wire guide remains in said first lumen of said dual lumen catheter add. .said dual lumen catheter remains within said endoscope such that said biliary duct may be visualized through the use of said contrast medium.

8. A method according to claim 7 wherein said contrast medium comprises a radio-opaque medium and said biliary duct is visualized radiologically.

9. A method for placing a biliary stent around a biliary calculus comprising the following steps:
    inserting a spring wire guide through an endoscope and into a biliary duct containing a biliary calculus;
    threading a biliary catheter over said spring wire guide and into said biliary duct containing said biliary calculus, said spring wire guide having a length greater than twice that of said biliary catheter;
    infusing a radio-opaque medium through said biliary catheter and into said biliary duct proximate to said biliary calculus such that said biliary calculus may be visualized radiologically;
    removing said biliary catheter from said endoscope and unthreading said biliary catheter from said spring wire guide such that the length of said spring wire guide permits said biliary catheter to be completely unthreaded from said spring wire guide while maintaining the position of said spring wire guide in said biliary duct; and
    threading a biliary stent over said spring wire guide and into biliary duct using a guiding catheter such that said stent is placed around said visualized biliary calculus.

10. A method for placing a stent around a pancreatic obstruction comprising the following steps:
    inserting a spring wire guide through an endoscope and into a pancreatic duct containing a pancreatic obstruction;
    threading a catheter over said spring wire guide and into said pancreatic duct containing said obstruction, said spring wire guide having a length greater than twice that of said catheter;
    infusing a radio-opaque medium through said catheter and into said pancreatic duct proximate to said obstruction such that said obstruction may be visualized radiologically;

removing said catheter from said endoscope and unthreading said catheter from said spring wire guide such that the length of said spring wire guide permits said catheter to be completely unthreaded from said spring wire guide while maintaining the position of said spring wire guide in said pancreatic duct; and threading a stent over said spring wire guide and into said pancreatic duct using a guiding catheter such that said stent is placed around said visualized obstruction.

11. A method for placing a stent around a cystic obstruction comprising the following steps:

inserting a spring wire guide through an endoscope and into a cystic duct containing a cystic obstruction;

threading a catheter over said spring wire guide and into said cystic duct containing said obstruction, said spring wire guide having a length greater than twice that of said catheter;

infusing a radio-opaque medium through said catheter and into said cystic duct proximate to said obstruction such that said obstruction may be visualized radiologically;

removing said catheter from said endoscope and unthreading said catheter from said spring wire guide such that the length of said spring wire guide permits said catheter to be completely unthreaded from said spring wire guide while maintaining the position of said spring wire guide in said cystic duct; and threading a stent over said spring wire guide and into said cystic duct using a guiding catheter such that said stent is placed around said visualized obstruction.

12. A method for placing a biliary stent around a biliary calculus through the use of a catheter having at least a first lumen and a second lumen, said first lumen having a wire guide threaded therethrough, and said wire guide having a length greater than twice that of said biliary catheter, comprising the following steps:

inserting said catheter and said wire guide through an endoscope and into a biliary duct containing a biliary calculus;

infusing a contrast medium through said second lumen of said catheter and into said biliary duct proximate to said biliary calculus such that said biliary calculus may be visualized through the use of said contrast medium;

removing said catheter from said endoscope and unthreading said catheter from said wire guide such that the length of said wire guide permits said catheter to be completely unthreaded from said wire guide while maintaining the position of said wire guide in said biliary duct; and threading a biliary stent over said wire guide and into biliary duct using a guiding catheter such that said stent is placed around said visualized biliary calculus.

13. A method for placing a stent around a pancreatic obstruction through the use of a catheter having at least a first lumen and a second lumen, said first lumen having a wire guide threaded therethrough, and said wire guide having a length greater than twice that of said catheter, comprising the following steps:

inserting said catheter and said wire guide through an endoscope and into a pancreatic duct containing a pancreatic obstruction;

infusing a contrast medium through said second lumen of said catheter and into said pancreatic duct proximate to said obstruction such that said obstruction may be visualized through the use of said contrast medium;

removing said catheter from said endoscope and unthreading said catheter from said wire guide such that the length of said wire guide permits said catheter to be completely unthreaded from said wire guide while maintaining the position of said wire guide in said pancreatic duct; and threading a stent over said wire guide and into said pancreatic duct using a guiding catheter such that said stent is placed around said visualized obstruction.

14. A method for placing a stent around a cystic obstruction through the use of a catheter having at least a first lumen and a second lumen, said first lumen having a wire guide threaded therethrough, and said wire guide having a length greater than twice that of said catheter comprising, the following steps:

inserting said catheter and said wire guide through an endoscope and into a cystic duct containing a cystic obstruction;

infusing a contrast medium through said second lumen of said catheter and into said cystic duct proximate to said obstruction such that said obstruction may be visualized through the use of said contrast medium;

removing said catheter from said endoscope and unthreading said catheter from said wire guide such that the length of said wire guide permits said catheter to be completely unthreaded from said wire guide while maintaining the position of said wire guide in said cystic duct; and threading a stent over said wire guide and into said cystic duct using a guiding catheter such that said stent is placed around said visualized obstruction.

* * * * *